United States Patent

Pracas

[11] Patent Number: 5,509,893
[45] Date of Patent: Apr. 23, 1996

[54] SPECULUM

[75] Inventor: Victor M. Pracas, Waroona, Australia

[73] Assignee: Meditech International Pty Ltd., Australia

[21] Appl. No.: 162,030

[22] PCT Filed: Jun. 5, 1992

[86] PCT No.: PCT/AU92/00261

§ 371 Date: Dec. 1, 1993

§ 102(e) Date: Dec. 1, 1993

[87] PCT Pub. No.: WO92/21279

PCT Pub. Date: Dec. 10, 1992

[30] Foreign Application Priority Data

Jun. 6, 1991 [AU] Australia .................................. PK6539
Feb. 3, 1992 [AU] Australia .................................. PL0637
Jun. 5, 1992 [WO] WIPO .............................. WO92/21279

[51] Int. Cl.⁶ ................................ A61B 1/00; A61B 1/32
[52] U.S. Cl. ........................... 600/224; 600/184; 600/214; 600/222
[58] Field of Search .................... 128/17, 18, 20, 128/3; 604/104, 105, 106, 107, 108, 109; 606/198; 600/184, 214, 222, 224

[56] References Cited

U.S. PATENT DOCUMENTS

| 167,666 | 9/1875 | Higbee | 128/17 |
| 672,239 | 4/1901 | Pilling | 128/17 |
| 1,412,975 | 4/1922 | Stanton | 604/108 |
| 2,083,573 | 6/1937 | Morgan | |
| 4,130,113 | 12/1978 | Graham | 128/20 |

FOREIGN PATENT DOCUMENTS

| 510677 | 12/1920 | France | 604/106 |
| 542744 | 8/1922 | France | 128/3 |
| 2490478 | 3/1982 | France | |
| 2708071 | 8/1978 | Germany | |
| 330629 | 6/1930 | United Kingdom | |

Primary Examiner—Richard J. Apley
Assistant Examiner—John P. Leubecker
Attorney, Agent, or Firm—Bachman & LaPointe

[57] ABSTRACT

A speculum having a dilator for insertion into a body cavity of a patient and an opening mechanism for opening the dilator to dilate the body cavity. The dilator has at least two dilator blade members which are pivotal. The opening mechanism consists of a collar which is rotatable to contact and bear against the blade members. This causes the blade members to pivot and move apart, thereby opening the dilator. This results in the body cavity of the patient being dilated which allows for easy examination thereof.

34 Claims, 10 Drawing Sheets

SPECULUM

The present invention relates to a speculum.

FIELD OF THE INVENTION

A speculum is an instrument for dilating a body cavity of a patient. Such cavity may be the vagina, rectum or ear, etc of the patient.

Conventional speculums are generally rather cumbersome to use requiring two handed operation. Additionally, they do not provide a uniform dilation of the body cavity, and they have a narrow rear opening. This makes visibility and instrument insertion cumbersome also. Further, they are generally made of metal, the cold surface of which can be quite uncomfortable for the patient.

The present invention provides a speculum which is relatively easy to use - insertion, dilation (opening), locking, unlocking and removal can all be effected with one hand. Insertion may be effected in a single movement. The speculum of the present invention may be made for left or right hand use.

The speculum of the present invention provides uniform dilation of the tissue of the body cavity to create relatively large dilation of the body cavity for visibility with improved comfort for the patient.

The speculum of the present invention is relatively compact and may be made from a light-weight material, e.g. plastics.

SUMMARY OF THE INVENTION

In accordance with one aspect of the present invention there is provided a speculum comprising:
  dilator means for insertion into a body cavity of a patient; and,
  opening means for opening said dilator means to dilate said body cavity, wherein said dilator means comprises at least two blade members which are pivotal and said opening means which is movable to contact and bear against said blade members to cause said blade members to pivot such that said dilator means opens to dilate said body cavity.

DESCRIPTION OF THE INVENTION

In FIG. 1 to 8 there is shown a speculum 10 in accordance with the present invention.

The speculum 10 shown in FIGS. 1 to 8 may be used for dilating the vagina of a patient, i.e. the speculum 10 shown in FIGS. 1 to 8 may be a vaginal speculum.

The speculum 10 comprises a dilator 12 for insertion into a body cavity, i.e. the vagina, of a patient and an opening mechanism, shown generally at 14, such that the dilator 12 may be opened to dilate the vagina of the patient.

The dilator 12 comprises (dilator) blade members 16a, 16b, 16c and 16d, collectively herein referred to as "blade members 16".

The dilator 12 of the speculum 10 shown in FIGS. 1 to 8 has four blade members 16.

For use as a vaginal speculum, it is preferable that four blade members 16 are provided.

However, other numbers of blade members 16 may be used for a vaginal speculum as will be later herein described.

Each of the blade members 16 comprises a proximal part 18 and a distal end 20. The blade members 16 are pivotally retained near their proximal parts 18 as will be later herein described.

Each of the blade members 16 has a rear portion 22 in the region of its proximal part 18. Each rear portion 22 has a forward part 23 which is substantially triangular. However, rather than the forward part 23 of each rear portion 22 tapering forwardly to an apex, a shank-like portion 24 projects or extends from each forward part 23. The shank-like portions 24 of the blade members 16a and 16b extend to rounded edges 26 which terminate the blade members 16a and 16b at their respective distal parts 20. The shank-like portions 24 of the blade members 16c and 16d extend to curved surface portions 28 which terminate the blade members 16c and 16d at their respective distal parts 20.

The blade members 16a and 16b are opposed, and the blade members 16c and 16d are opposed.

The blade member 16d has a small notch 30 at its distal part 20, adjacent its curved surface portion 28. The blade members 16c and 16d are longer than the blade members 16a and 16b. The blade member 16c is slightly longer than the blade member 16d.

Each of the blade members 16 is curved in its transverse direction. The direction of this curvature is represented by the double arrow T in FIG. 2.

Figure 1:
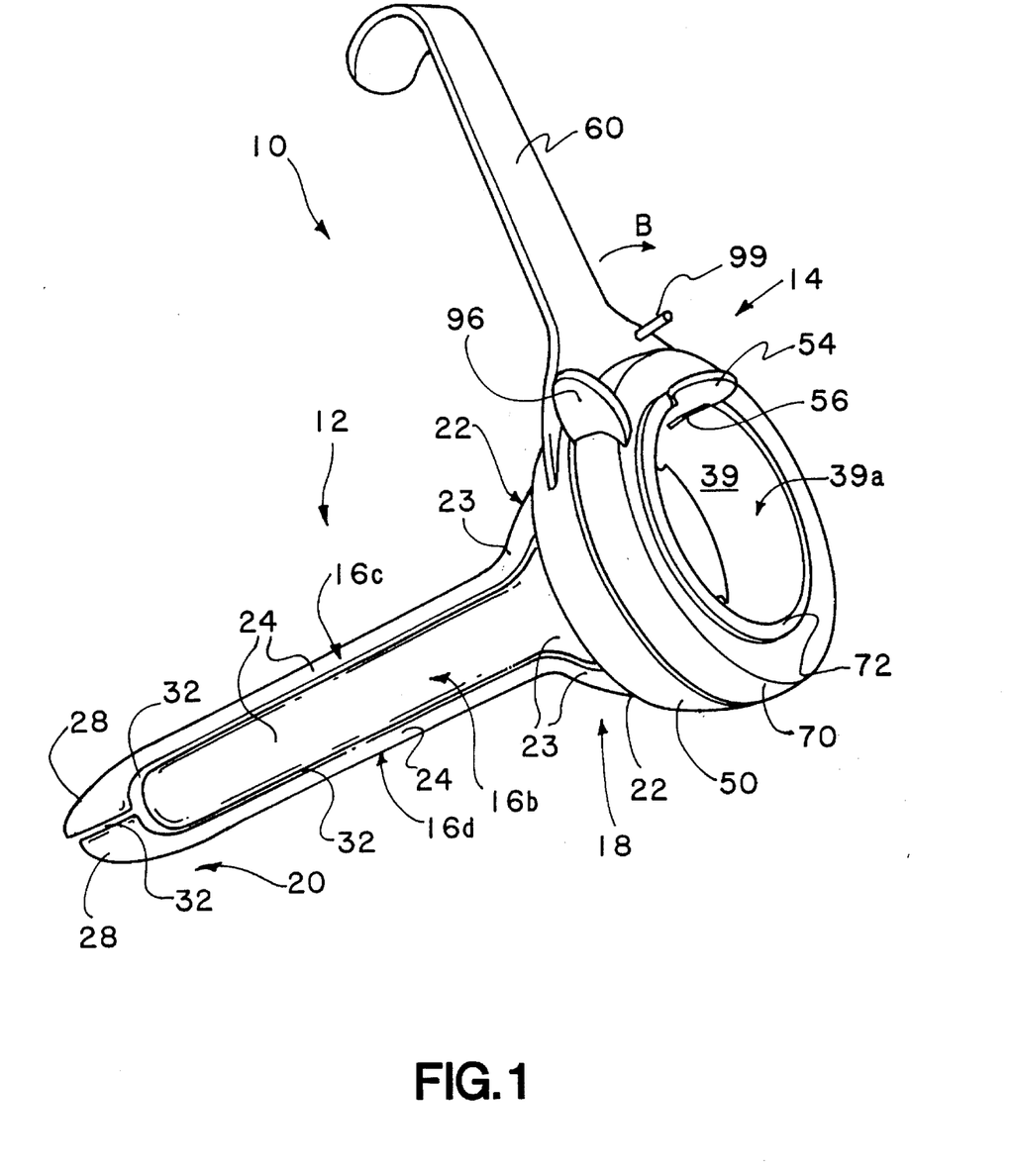
FIG. 1 is a first perspective view of a first embodiment of a speculum in accordance with the present invention, showing the dilator closed.
Figure 3:
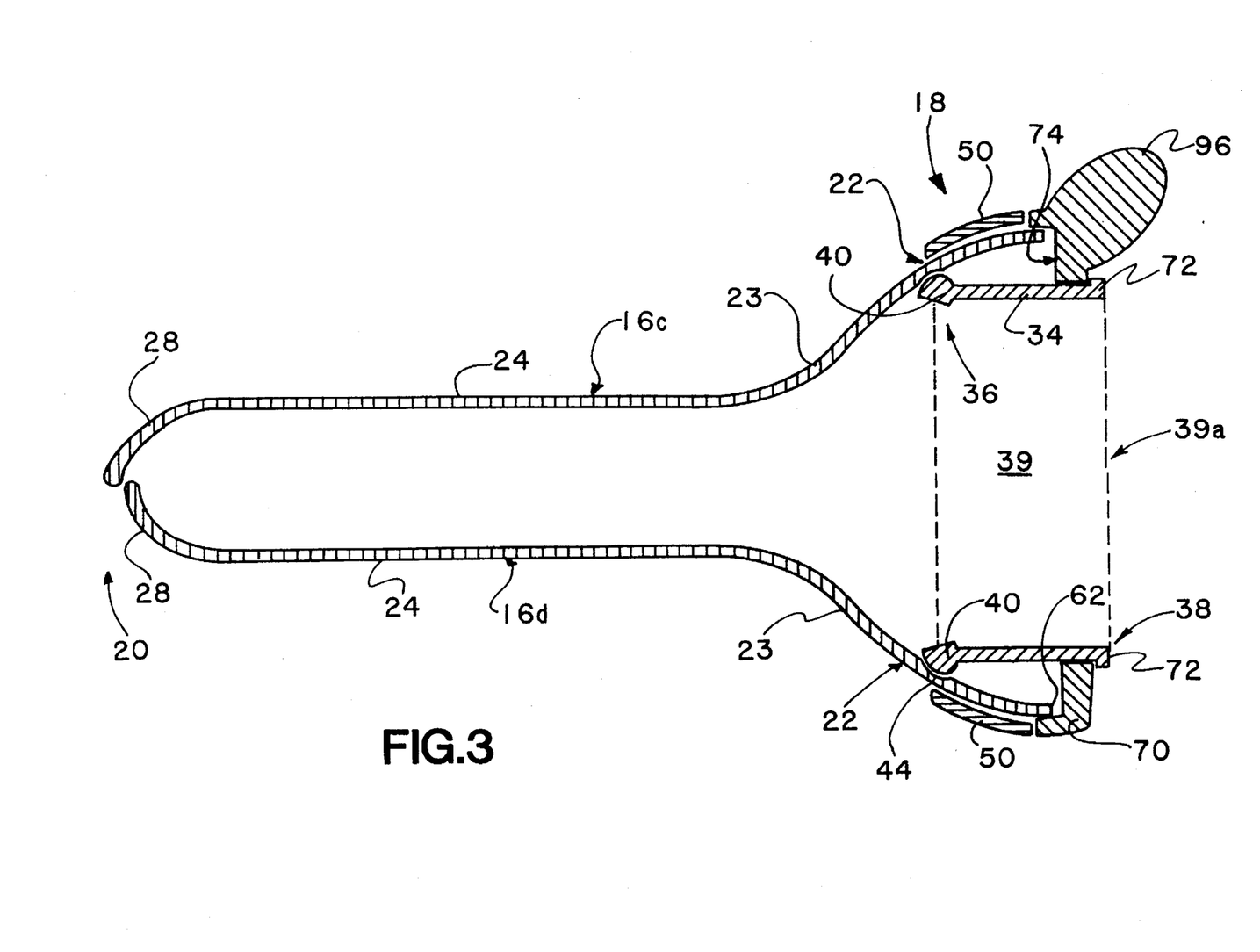
FIG. 3 is a sectional side elevation view of the speculum shown in FIG. 1 with the dilator closed.

The curved surface portions 28 of the blade members 16c and 16d are arranged such that when the dilator 12 is closed (shown in FIGS. 1 and 3), the curved surface portions 28 define a rounded dome-like surface as can be seen in FIGS. 1 and 3. The curved surface portions 28 of the blade members 16c and 16d extend beyond the rounded edges 26 of the blade members 16a and 16b to form the rounded dome-like surface hereinabove described.

The blade members 16 are arranged such that when the dilator 12 is closed, the forward parts 23 of the rear portions 22 define a substantially dome-like shaped form with the shank-like portions 24 extended therefrom in a substantially tubular form, as is best seen in FIG. 1. The blade members 16 are arranged such that even when the dilator 12 is closed, there are still gaps 32 between adjacent blade members 16.

The notch 30 in the blade member 16d ensures that a gap 32 also exists between the edges of the curved surface portions 28 of the blade members 16c and 16d. The blade members 16 of the dilator 12 are pivotally retained as will be now described.

Figure 4:
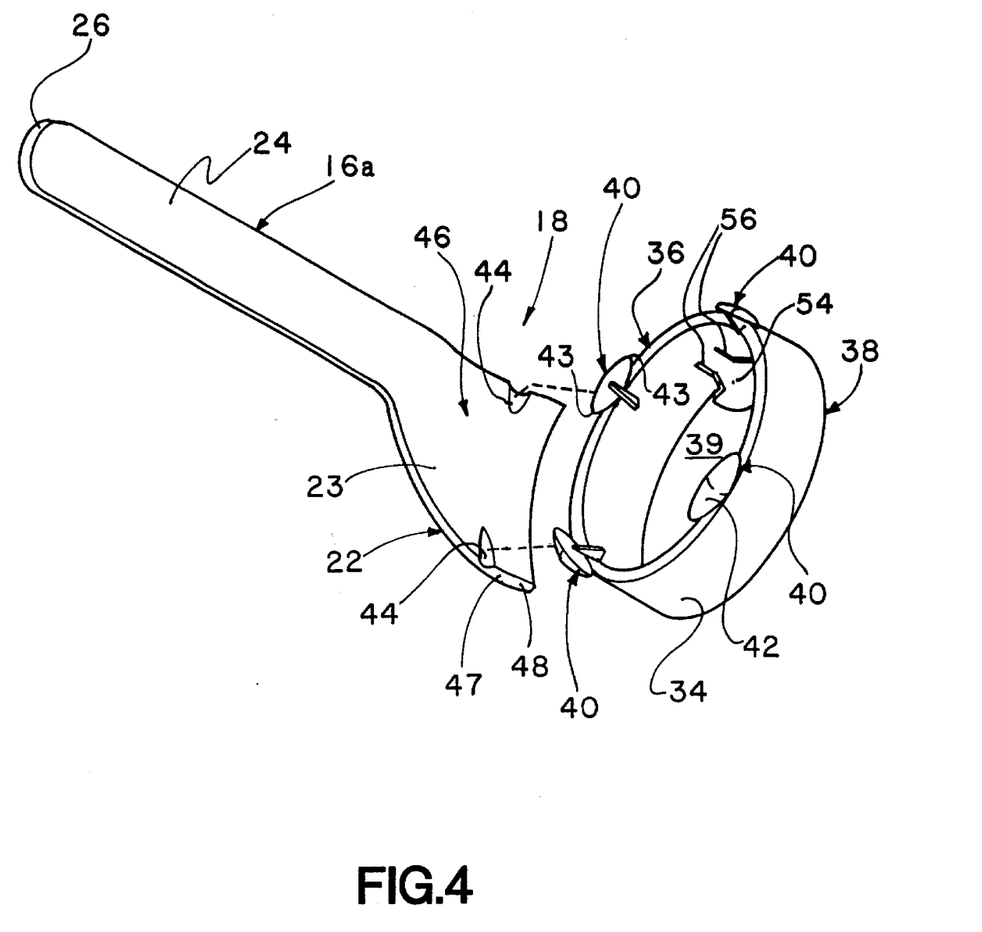
FIG. 4 is an exploded perspective view showing a blade member and the tubular member of the speculum shown in FIG. 1.

FIG. 4 shows the arrangement which enables pivotal movement of the blade members 16. However, in FIG. 4 only the blade member 16a has been shown for clarity of representation.

The blade members 16 are pivotally supported by a support member 34 having a first (forward) end 36 and a second (rear) end 38. The support member 34 is of substantially short tubular form. The support member 34 defines a passage 39 therethrough, and an opening 39a at the rear of the speculum 10. The blade members 16 extend outwardly from the support member 34 in side by side, or adjacent, manner when the dilator 12 is closed.

The support member 34 is provided with lug-like members 40 at the first end 36. The lug-like members 40 are spaced around the edge of the support member 34 at the first end 36.

The lug-like members 40 have curved surfaces 42 such that the lug-like members 40 are of an approximately semi-ellipsoidal shape. The curved surfaces 42 slope away from the central region of the lug-like members 40 to rounded apexes 43 on either side in the circumferential direction of the support member 34.

The rear portion 22 of each blade member 16 is provided with a recess 44 on its inside face 46 adjacent respective side edges 47 at its proximal part 18.

The lug-like members 40 and recesses 44 are contoured such that the recesses 44 of each blade member 16 mate with respective lug-like members 40. This is shown in FIG. 4. Each recess 44 of each blade member 16 mates, or sits, on half a lug-like member 40. In this way, adjacent blade members 16 sit on respective halves of a lug-like member 40 such that the blade members 16 are pivotally supported by the support member 34.

The side edges 47 of each of the rear portion 22 (of each blade members 16) taper slightly toward the termination of the rear portion 22 of each blade member 16. These tapered edges are shown by reference numeral 48 in FIGS. 4 and 5. A collar 50 is provided around the blade members 16 over their rear portions 22. The collar 50 surrounds the rear portions 22 between the recesses 44 and the terminations of the rear portions 22. Connecting ribs 52 (best seen in FIG. 5) extend from the support member 34 to the collar 50. The connecting ribs 52 are positioned between respective adjacent blade members 16. The tapered edges 48 form spaces between the side edges 47 of adjacent blade members 16 where the connecting ribs 52 may be provided. The connecting ribs 52 connect the support member 34 and the collar 50.

In this way, the blade members 16 are pivotally supported on the support member 34, around the periphery thereof, by the collar 50, with the blade members 16 extending outwardly therefrom.

The lug-like members 40 and the matching contoured recesses 44 of the blade members 16 permit pivotal movement of the blade members 16. Thus, the lug-like members 40 act as pivotal fulcrums. The connecting ribs 52 connect the support member 34 and the collar 50 to ensure that the blade members 16 are retained in position with respect to the support member 34.

The support member 34 is also provided with a lug 54 at the second end 38. The lug 54 serves as a thumb grip and projects rearwardly of the support member 34. A pair of incisions 56 extend from the lug 54 in the support member 34 a short distance. This permits the lug 54 to be depressed slightly and then return to its position shown in FIG. 5 when released.

Figure 5:
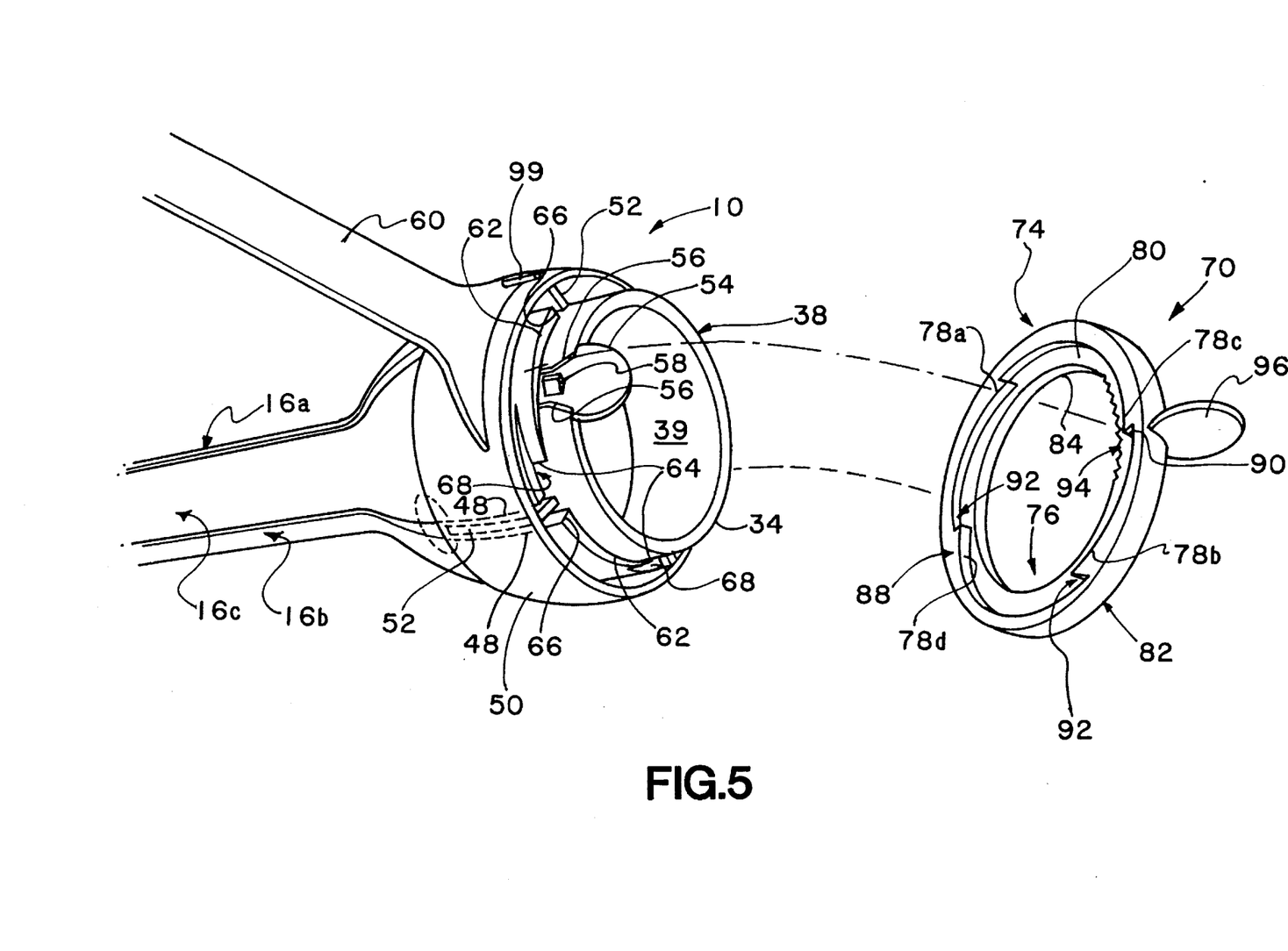
FIG. 5 is a partly exploded perspective view of the rear of the speculum shown in FIG. 1.

A pawl member 58 is provided just forwardly of the lug 54, between the incisions 56.

A handle 60 is provided on the collar 50. The handle 60 extends radially from the collar 50.

The rear portions 22 of the blade members 16 each terminate in a substantially wedge shaped portion 62.

The substantially wedge shaped portions 62 extend in the transverse direction T of the blade members 16.

The substantially wedge shaped portions 62 each taper in the same direction to a respective tip 64. In FIG. 5, this direction is shown as a counter-clockwise direction. Each of the substantially wedge shaped portions 62 has a base 66 at an edge of the termination of the rear portion 22 of a blade member 16. The bases 66 are angled. The substantially wedge shaped portions 62 taper to the tips 64 spaced from the bases 66. The substantially wedge shaped portions 62 extend in the transverse direction T of the blade members 16 to substantially half way around the terminating edge of the rear portions 22 of the blade members 16 where they terminate in the tips 64.

A cut-away portion 68 is provided in each of the blade members 16 adjacent the tip 64 such that the substantially wedge shaped portions 62 form the extremities of the rear portions 22 of the blade members 16 at the proximal parts 18.

The opening mechanism 14 comprises a movable collar 70.

The movable collar 70 is provided around the support member 34, near its second end 38.

The support member 34 is provided with a flange 72 (shown in FIG. 3) at its second end 38 which retains the movable collar 70 in place on the support member 34. The movable collar 70 has an inside (front) face 74 (visible in FIGS. 5 and 6) which is provided with a cam like arrangement 76. The inside face 74 is the one that faces the substantially wedge shaped portions 62 of the blade members 16. This can be seen in FIGS. 5 and 6.

The cam-like arrangement 76 comprises arcuate portions 78a, 78b, 78c and 78d (collectively referred to as "arcuate portions 78") which are raised above a lower surface 80. The arcuate portions 78 curve inwardly in the direction from near the outer side 82 toward near the inner side 84 of the movable collar 70. The direction of this inward curving of the arcuate portions 78 is clockwise a seen in FIG. 6.

Each arcuate portion 78 forms a tip 86 at its forward end 88 with a rear surface 90 of an adjacent arcuate portion 78. The rear surface 90 of each arcuate portion 78 is angled such that it forms an angled recess 92 with the remainder of the arcuate portion 78.

The arcuate portions 78 are arranged such that the arcuate portions 78a and 78b have the same curvature. The arcuate portion 78c has a greater curvature than the arcuate portions 78a and 78b such that the tip 86 of the arcuate portion 78c is closer to the inner side 84 of the movable collar 70 than the tips 86 of the arcuate portions 78a and 78b. The arcuate portion 78d, in turn, has a greater curvature than the arcuate portion 78c (and the arcuate portions 78a and 78b) such that the tip 86 of the arcuate portion 78d is closer to the inner side 84 of the movable collar 70 than the tip 86 of the arcuate portion 78c and the tips 86 of the arcuate portions 78a and 78b). The arcuate portions 78a, 78b, 78c and 78d operatively cooperate with blade members 16a, 16b, 16c and 16d, respectively, to open the dilator 12. This will be later described.

The movable collar 70 is also provided with a ratchet arrangement 94 and a thumb operable handle 96. The ratchet arrangement 94 is provided on the inner side 84 of the movable collar 70 and the handle 96 projects from the outer side 82 of the movable collar 70. The handle 96 is arranged such that it projects radially outwardly from the movable collar 70 in the region of the rear part of the arcuate portion 78b, i,e. near its rear surface 90.

The ratchet arrangement 94 is positioned such that, viewed from the inside face 74 of the movable collar 70, it is positioned beneath the handle 96, extending a short distance beyond the handle 96 on the right and extending a greater distance on the left to approximately half the length of the arcuate portion 78c.

In the position of the movable collar 70 shown in FIG. 1, i.e. when the dilator 12 is closed, the substantially wedge shaped portions 62 are positioned such that the (angled) bases 66 of the substantially wedge shaped portions 62 are close to, or in abutment with, respective rear surfaces 90 that form the angled recesses 92. In this position, the (angled) bases 66 are engaged in the angled recesses 92, thereby preventing any pivotal movement of the blade members 16. This position of the substantially wedge shaped portions 62 is exemplified in broken lines by arrow A in FIG. 6 which shows the position of the substantially wedge shaped portion 62 of the blade members 16b.

Figure 2:
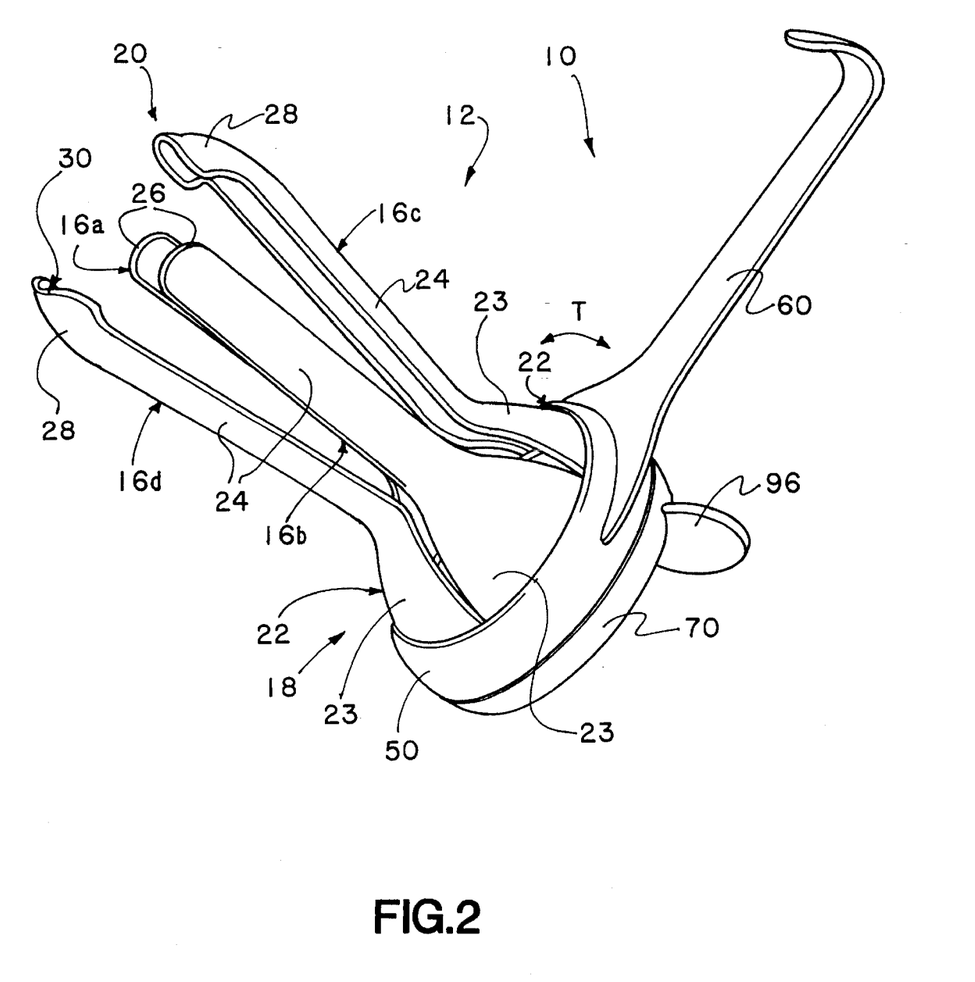
FIG. 2 is a second perspective view of the speculum shown in FIG. 1, showing the dilator open.
Figure 6:
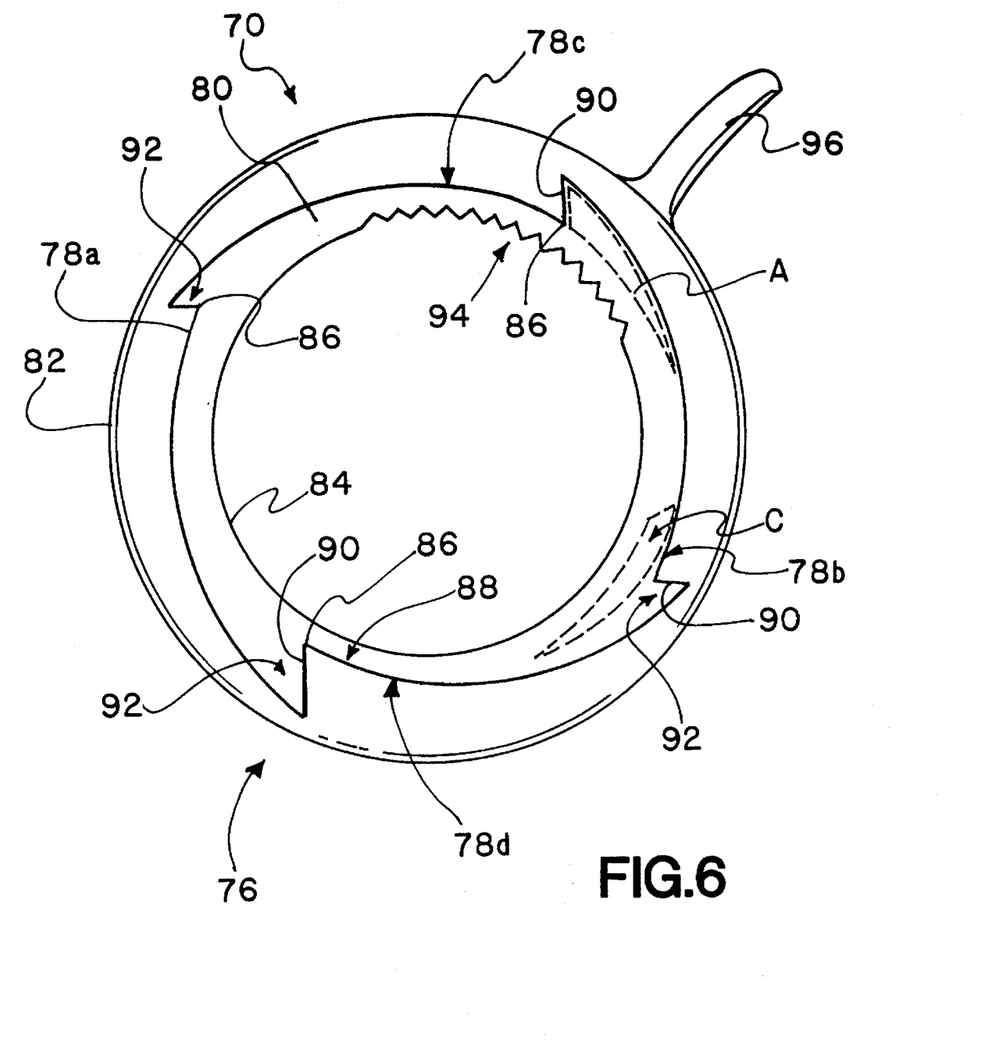
FIG. 6 is a front elevation view of the movable collar of the speculum shown in FIG. 1.
Figure 7:
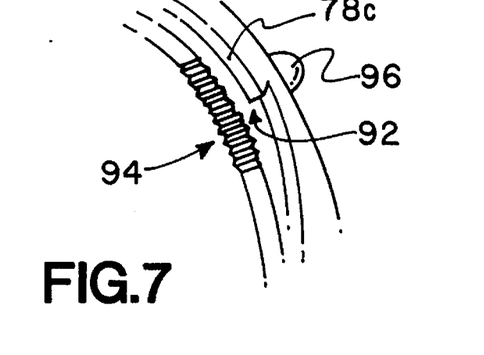
FIG. 7 is a detail perspective view of the ratchet arrangement of the movable collar.
Figure 8:
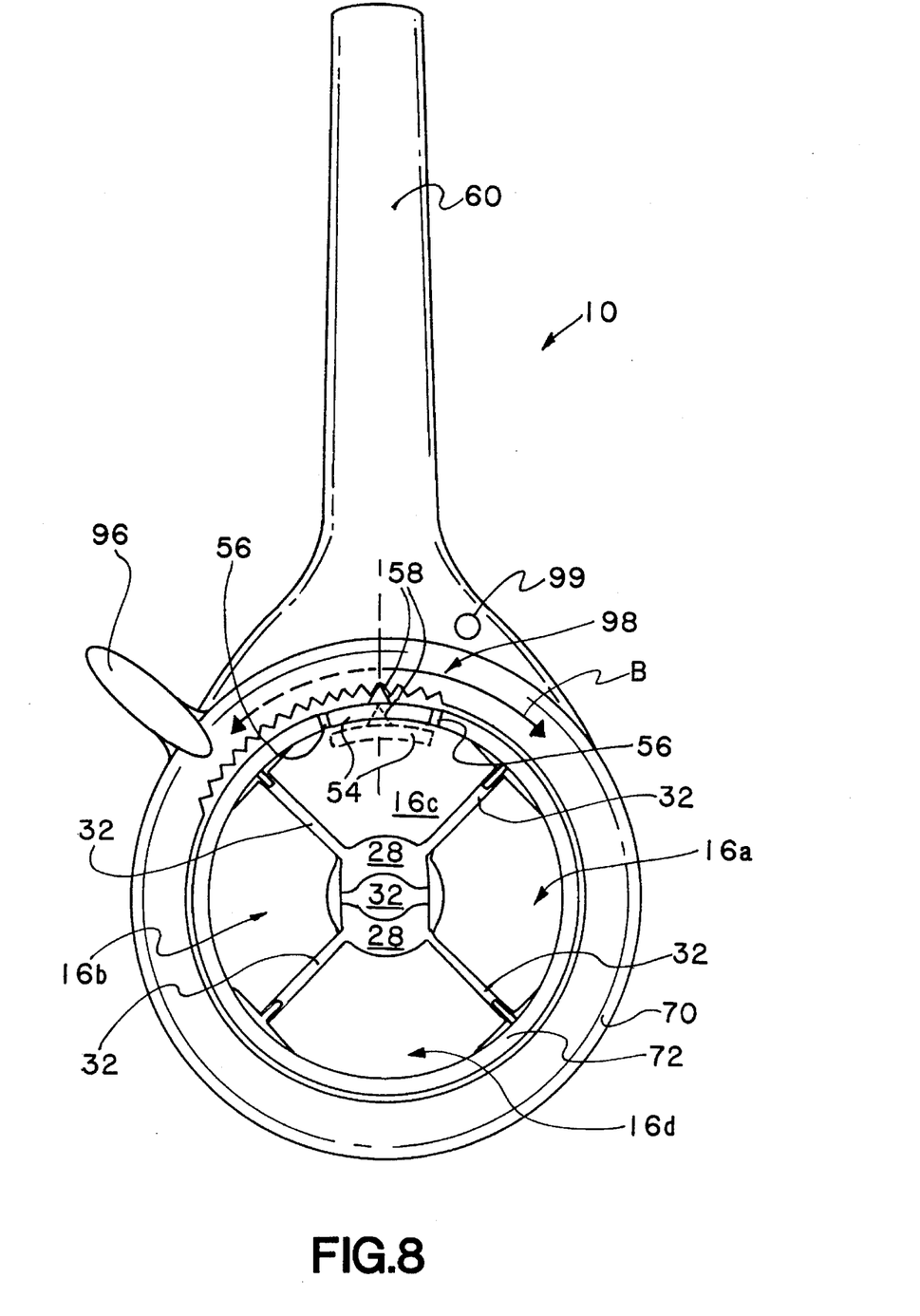
FIG. 8 is a rear elevation view of the speculum shown in FIG. 1.

When the movable collar 70 is moved to the position shown in FIG. 2 (by moving the handle 96 in the direction shown by arrow B in FIG. 1), the relative positioning of the substantially wedge shaped portions 62 of the blade members 16 is exemplified by arrow C in FIG. 6. FIG. 6 shows the position of the substantially wedge shaped portion 62 of the blade member 16b. This will be further herein described.

The speculum 10 further comprises a locking mechanism 98. The locking mechanism 98 comprises the pawl 58 and ratchet arrangement 94.

When the pawl 58 engages with the ratchet arrangement 94, the movable collar 70 is locked against movement in the direction opposite to the arrow B.

The pawl 58 is angled such that the ratchet arrangement 94 allows the movable collar 70 to be readily rotated in the direction shown by arrow B in FIG. 1, (to open the dilator 12) but prevents movement in the reverse direction (to close the dilator 12) unless the pawl 58 is disengaged from the ratchet arrangement 94. A pin 99 is provided to limit the travel of the movable collar 70 in the direction B. The pin 99 extends form the base of the handle 60. The handle 96 abuts with the pin 99 to thereby limit travel of the movable collar 70.

Preferably, the speculum 10 is made of light-weight material, e.g. plastics.

Preferably, the speculum 10 is made of transparent material, e.g. clear plastics.

Figure 9:
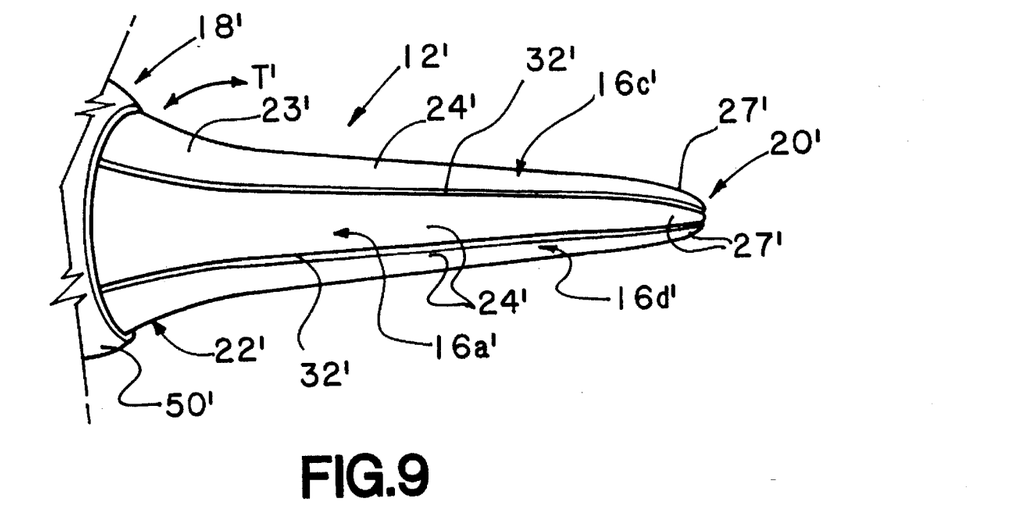
FIG. 9 is a first perspective view of the dilator of a second embodiment of a speculum in accordance with the present invention, showing the dilator closed.
Figure 10:
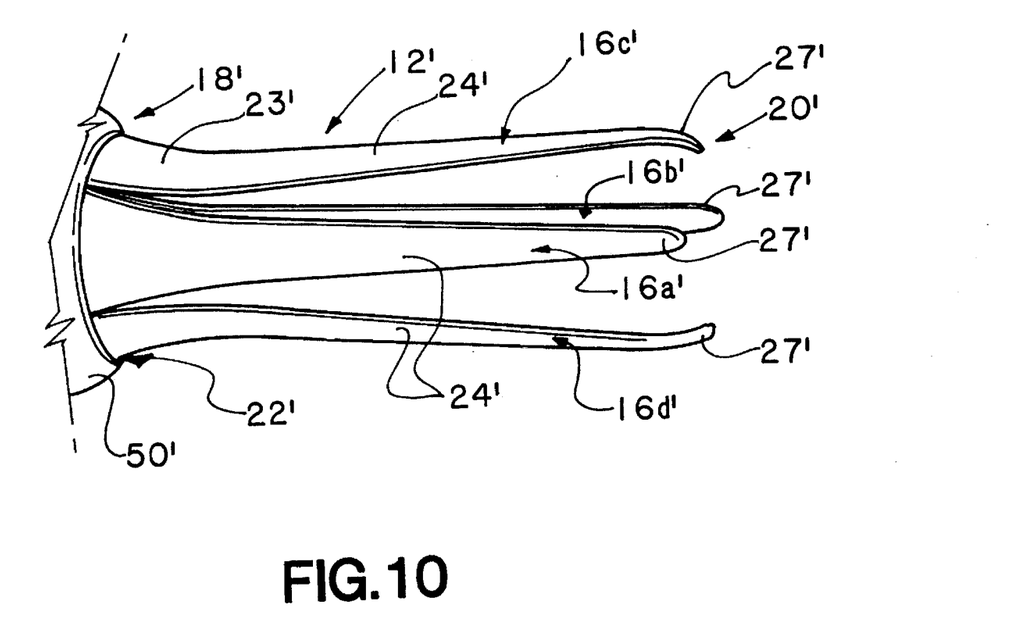
FIG. 10 is a second perspective view of the dilator shown in FIG. 9, showing the dilator open.

FIGS. 9 and 10 show the dilator 12' of a second embodiment of a speculum in accordance with the present invention. The same reference numerals are used in relation to the speculum of the second embodiment as are used for the speculum 10 of the first embodiment to denote corresponding parts. However, in referring to the speculum of the second embodiment a superscript (') follows the numbers to enable the embodiments to be readily distinguished.

The speculum of the second embodiment is substantially the same as the speculum 10 of the first embodiment except for the dilator 12'. Accordingly, only the dilator 12' of the speculum of the second embodiment is shown in FIGS. 9 and 10, and the following description will be limited to the features of difference of the dilator 12'. However, it is to be understood that the remainder of the speculum of the second embodiment is substantially the same as the speculum 10 of the first embodiment hereinbefore described. The dilator 12' comprises (dilator) blade members 16a', 16b', 16c' and 16d', collectively referred to as "blade members 16'".

The blade members 16' have a structure different from that of the blade members 16 of the speculum 10. The forward part 23' of the rear portion 22' of each blade member 16' has a gentler taper from which a shank-like portion 24' extends. The remainder of the rear portion 22' of each blade member 16' is the same as that of the rear portions 22 of the blade members 16 of the speculum 10. The shank-like portions 24' of the blade menders 16' extend in a (longitudinally) tapering manner from respective forward portions 23' to a narrower tip 27' at the distal parts 20' of the blade members 16'. The narrower tip 27' of each blade member 16' itself curves inwardly (in a transverse direction).

The blade members 16' are of the same size and length. The blade members 16' are arranged such that when the dilator 12' is closed (shown in FIG. 9) the dilator 12' is substantially in the space of a cone. The base of this cone is comprised of the forward parts 23' of the rear portions 22' of the blade members 16' and the apex is formed by the tips 27' of the blade members 16' at the distal ends 20'. This apex is rounded since the narrower tips 27' of the blade members 16' at their distal ends 20' curve inwardly.

Each of the blade members 16' is also curved in the transverse direction T.

In this way, the blade members 16' define the cone shape referred to above.

The blade members 16' are positioned such that even when the dilator 12' is in its closed position (as shown in FIG. 1) there is still a gap 32' between adjacent blade members 16'.

Figure 11:
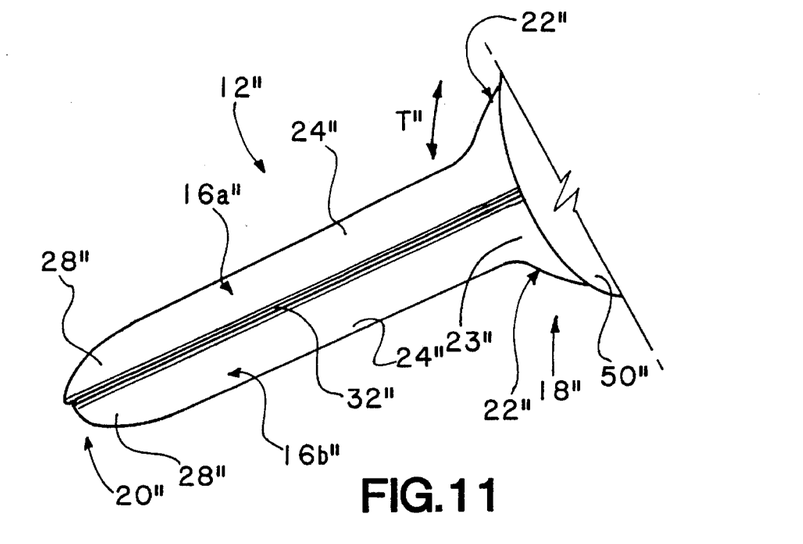
FIG. 11 is a perspective view of the dilator of a third embodiment of a speculum in accordance with the present invention showing the dilator closed.
Figure 12:
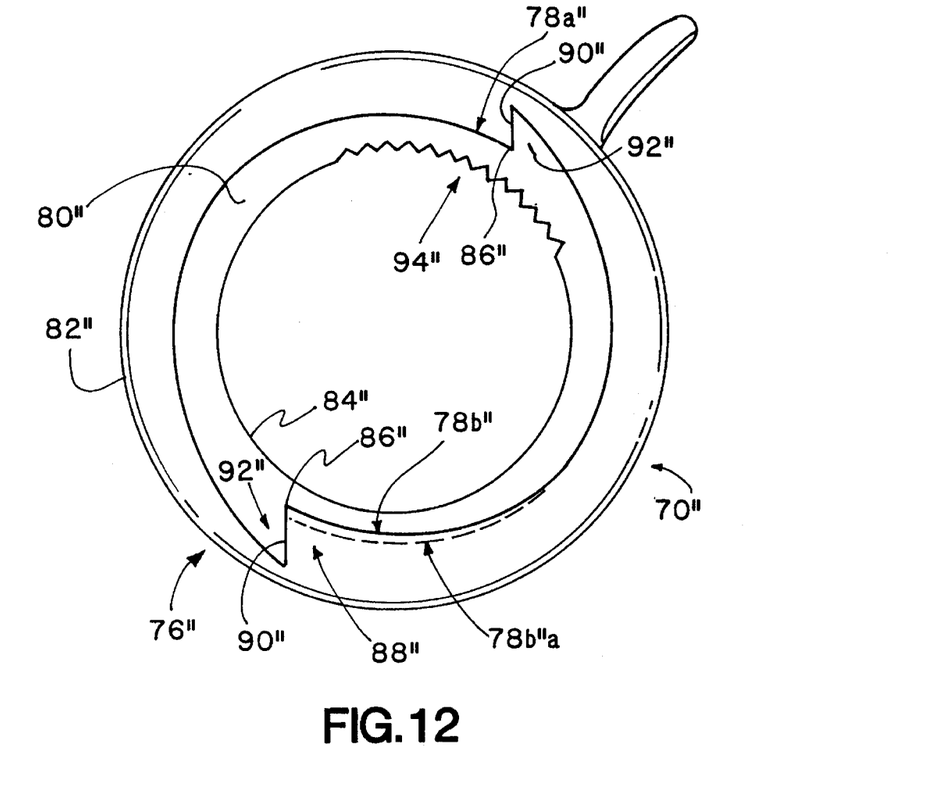
FIG. 12 is a front elevation view of the movable collar of the speculum of the third embodiment.

FIG. 11 and 12 show the dilator 12" and the movable collar 70", respectively, of a third embodiment of a speculum in accordance with the present invention. The same reference numerals are used in relation to the speculum of the third embodiment as are used for the speculum 10 of the first embodiment to denote corresponding parts. However, in referring to the speculum of the third embodiment a double superscript (") follows the numbers to enable the embodiments to be readily distinguished. The speculum of the third embodiment is substantially the same as the speculum 10 of the first embodiment. The major differences are in the dilator 12" and the cam-like arrangement 76" of the movable collar 70".

Accordingly, only the dilator 12" and the movable collar 70" of the speculum of the third embodiment are shown in FIGS. 11 and 12, and the following description will be generally limited to the features of difference of the dilator 12" and the cam-like arrangement 76" of the movable collar 70".

However, it is to be understood that the remainder of the speculum of the third embodiment is substantially the same as the speculum 10 of the first embodiment hereinbefore described.

The dilator 12" has only two (dilator) blade members 16a' and 16b" (collectively referred to as "blade members 16"") and the cam-like arrangement 76" has only two arcuate portions 78a" and 78b". (Accordingly, only two lug-like members 40" (obscured) are provided on the support member 34" (obscured).

The blade members 16" have a structure different from that of the blade members 16 of the speculum 10.

The blade members 16a" and 16b" can be considered as consisting, respectively, of one of the blade members 16c and 16d (of the Speculum 10) and half of each of the blade members 16a and 16b (of the speculum 10).

Accordingly, the forward parts 23" of the rear portion 22" of each blade member 16" is substantially semi-dome in shape with the shank- like portions 24" extending therefrom. When the dilator 12" is closed, these forward parts 23" together define a substantially dome-like shaped form, with the shank-like portions 24" extending therefrom in a substantially tubular form.

The shank-like portions 24" of the blade members 16" extend from respective forward portions 23" to curved surface positions 28" at the distal parts 20" of the blade members 16".

The blade member 16b" has a small notch (obscured) (corresponding to the notch 30 of the blade member 16d of the speculum 10) adjacent its curved surface portion 28". The blade member 16b" is slightly longer than the blade member 16a".

Each of the blade members 16" is curved in its transverse direction T".

The curved surface portions 28" are arranged such that they define a rounded dome-like surface when the dilator 12" is closed.

The remainder of the blade members 16", i.e. the rear portions 22", is similar to the blade members 16 of the speculum 10, except that the rear portions 22" are approximately twice the length in the transverse direction T" as the rear portions 22 (of the speculum 10). Since the dilator 12" of the speculum of the third embodiment has two blade members 16", the cam-like arrangement 76" has two arcuate portions 78a' and 78b".

The arcuate portions 78a" and 78b" operatively cooperate with the blade members 16a" and 16b", respectively, to open the dilator 12".

The arcuate portion 78b" has a greater curvature than the arcuate portion 78a", such that the tip 86" of the arcuate portion 78b" is closer to the inner side 84" of the movable collar 70" than the tip 86" of the arcuate portion 78a'.

FIG. 12 shows an alternative curvature for the arcuate portion 78b" in broken lines 78b"a. The arcuate portion 78b"a has the same curvature as the arcuate portion 78a".

Figure 13:
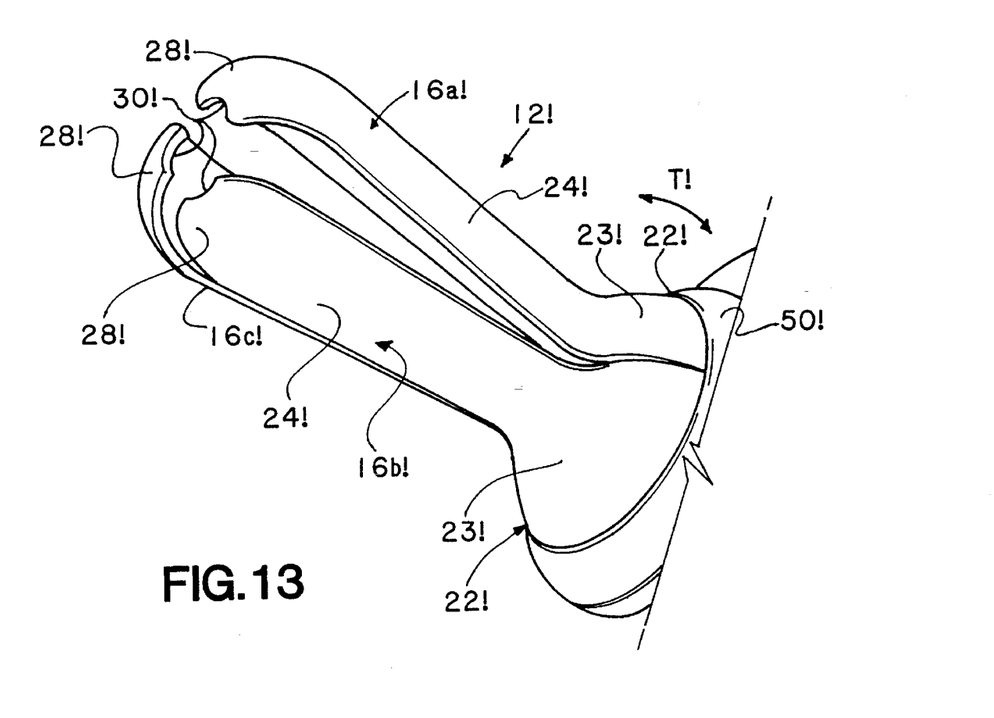
FIG. 13 is a perspective view of the dilator of a fourth embodiment of a speculum in accordance with the present invention showing the dilator partly open; and, FIG. 14 is a front elevation view of the movable collar of the speculum of the fourth embodiment.
Figure 14:
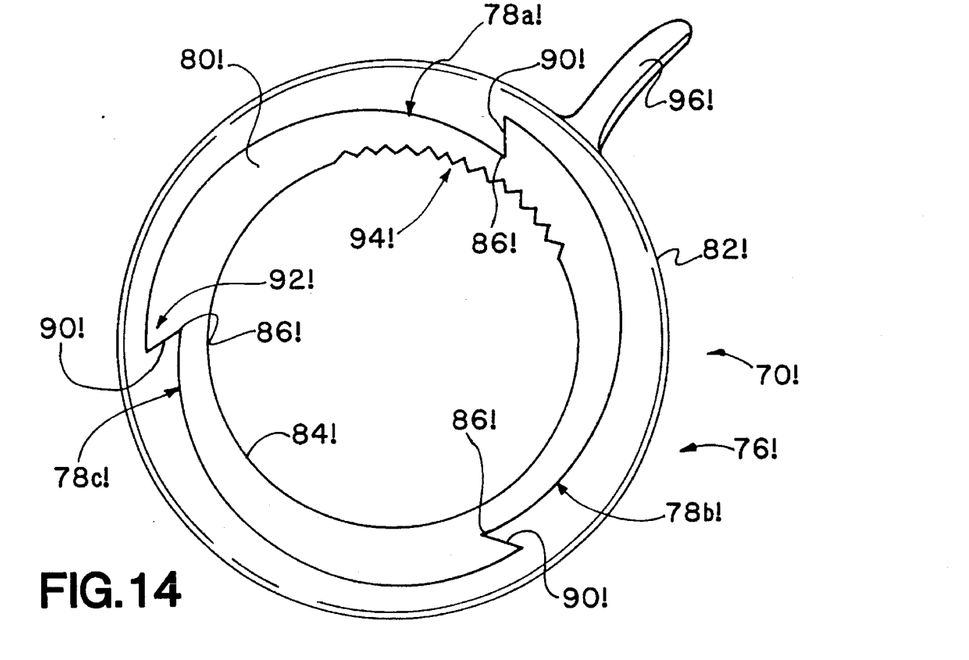

FIGS. 13 and 14 show the dilator 12! and the movable collar 70!, respectively, of a fourth embodiment of a speculum in accordance with the present invention.

The same reference numerals are used in relation to the speculum of the fourth embodiment as are used for the speculum of the first embodiment to denote corresponding parts. However, in referring to the speculum of the fourth embodiment an exclamation mark (!) follows the numbers to enable the embodiments to be readily distinguished.

The speculum of the fourth embodiment is substantially the same as the speculum 10 of the first embodiment. The major differences are in the dilator 12! and the cam-like arrangement 76! of the movable collar 70!. Accordingly, the dilator 12! and the movable collar 70! of the speculum of the fourth embodiment are shown in FIGS. 13 and 14, and the following description will be generally limited to the features of difference of the dilator 12! and the cam arrangement 76! of the movable collar 70!. However, it is to be understood that the remainder of the speculum of the fourth embodiment is substantially the same as the speculum 10 of the first embodiment hereinbefore described.

The dilator 12! has three (dilator) blade members 16a!, 16b! and 16c! (collectively referred to as "blade members 16!), and the cam arrangement 76! has three arcuate portions 78a!, 78b! and 78c! (Accordingly, only three lug-like members 40! (obscured) are provided on the support member 34! (obscured).

The blade members 16! have a structure different from that of the blade members 16 of the speculum 10. Each rear portion 22! of the blade members 16! has a forward part 23! which is substantially triangular (though of a size different from the forward part 23 of the speculum 10 ) with the shank- like portions 24 ! extending therefrom. When the dilator 12! is closed, these forward parts 23! together define a substantially dome-like shaped form, with the shank-like portions 24! extending therefrom in a substantially tubular form.

The shank-like portions 24! of the blade members 16! extend from respective forward parts 23! to curved surface, portions 28! at the distal parts 20! of the blade members 16! One or more of the blade members 16a!, 16b! and 16c! may be provided with a small notch 30! adjacent its curved surface portion 28!

The blade members 16a!, 16b! and 16c! are the same. Each blade member 16! is curved in its transverse direction T!

The curved surface portions 28! define a rounded dome-like surface when the dilator 12! is closed. The remainder of the blade members 16!, i.e. the rear portions 22!, is similar to the blade members 16 of the. speculum 10, except that the rear portions 22! are of a larger size than the rear portions 22 (of the speculum 10) but smaller than the rear portions 22" (of the speculum of the third embodiment).

Since the dilator 12! of the speculum of the fourth embodiment has three blade members 16!, the cam arrangement 76! has three arcuate portions 78a!, 78b! and 78c! The arcuate portions 78a!, 78b! and 78c! operatively cooperate with the blade members 16a!, 16b! and 16c!, respectively, to open the dilator 12!

The arcuate portions 78a!, 78b! and 78c! have the same curvature. In this way, the tips 86! of the arcuate portions 78a!, 78b! and 78c! are equally spaced from the inner side 84! of the movable collar 70!

The manner of use and operation of the speculum of the present invention will now be described, with particular reference to the speculum of the first embodiment. The following description will be with reference to use of the speculum 10 as a vaginal speculum.

The speculum 10 may, for example, be used by a user, e.g. medical practitioner, as a vaginal speculum in connection with the examination of, or carrying out a medical procedure on, a female patient. Such examination, for example, may be in relation to the cervix of the patient. The speculum 10 is used to dilate the vagina of the patient.

The medical practitioner holds the speculum 10 by gripping the handle 60 in his/her left hand with the blade member 16c uppermost and the handle 96 in the position shown in FIG. 1. In this position, the dilator 12 is closed and the bases 66 of the substantially wedge shaped portions 62 (of the blade members 16) are in abutment with the surfaces 90 to ensure that the dilator 12 remains closed. This is exemplified in FIG. 6 by the arrow A which shows the position of the substantially wedge shaped portion 62 of the blade member 16b relative to the arcuate portion 78b.

The medical practitioner then inserts the end of the dilator 12 defined by the distal parts 20 of the blade members 16 into the opening of the vagina of the patient. The dilator 12 is inserted into the vagina the required distance. The dilator 12 is inserted into the patient's vagina such that the blade member 16c is uppermost, the blade member 16d lowermost, and the blade members 16a and 16b at the sides.

Since the wall of the patient's vagina has a natural tendency to remain collapsed, the blade members 16 are in close contact with the walls of the vagina of the patient. Once the dilator 12 has been inserted into the patient's vagina the appropriate distance, the medical practitioner pushes on the handle 96 (using the thumb of his/her left hand) in direction of arrow B shown in FIG. 1. This causes the movable collar 70 to move, i.e. in the same direction B, which the pawl 58 and the ratchet arrangement 94 allow.

As the movable collar 70 is moved in the direction shown by arrow B in FIG. 1, the arcuate portions 78 of the movable collar 70 bear against the rear portions 22 of the blade members 16 at the substantially wedge shaped portions 62 and push against them. This is exemplified in FIG. 6 by the arrow C which shows the position of the substantially wedge shaped portion 62 of the blade member 16b relative to the arcuate portion 78b.

This action on the blade members 16 causes the blade members 16 to pivot by way of the recesses 44 and the lug-like members 40. The blade members 16 begin to separate and open (i.e. the dilator 12 opens) against the tendency of the wall of the vagina (of the patient) to remain collapsed.

When the dilator 12 has been opened an appropriate amount, the medical practitioner ceases pushing on the handle 96. This stops the movable collar 70 from continuing to move, i.e. rotate, in the direction of arrow B. Further, the pawl 58 and ratchet arrangement 94 prevent the movable collar 70 from moving in the opposite direction. This keeps the movable collar 70 and blade members 16 in the set position with the dilator 12 open. Thus, the pawl 58 and ratchet arrangement 94 prevent the wall of the vagina (of the patient) from collapsing to close the dilator 12. The dilator 12 is opened until the blade members 16 dilate the patient's vagina an appropriate amount, having regard to the action, or procedure, to be performed by the medical practitioner and the comfort of the patient.

Due to the arrangement of the substantially wedge shaped members 62 and the curvatures of the arcuate portions 78, the blade members 16 open by different amounts upon rotation of the movable collar 70 in the direction of arrow B.

As previously hereinbefore described, the curvature of the arcuate portions 78a and 78b is the same. As the movable collar 70 is rotated in the direction of arrow B, the arcuate portion 78a and 78b act on the blade members 16a and 16b, respectively. However, since the arcuate portions 78a and 78b are of a lesser curvature, they force the blade members 16a and 16b to pivot to a lesser extent and so the blade members 16a and 16b open a relatively small amount. Thus, the blade members 16a and 16b reach their maximum opening before the blade members 16c and 16d and before the movable collar 70 has moved through its maximum travel. The arcuate portion 78c has a greater curvature than the arcuate portions 78a and 78b and so it acts on the blade member 16c for a relatively greater proportion of the travel of the movable collar 70. This causes the blade member 16c to continue opening, even after the blade members 16a and 16b have ceased to open. Since the arcuate portion 78d is of the greatest curvature, it continues to act on the blade member 16d thereby further opening the blade member 16d, even after the other blade member 16a, 16b and 16c have ceased to open notwithstanding that the movable collar 70 is still being rotated in the direction of arrow B.

Thus, the blade member 16d opens the greatest amount followed by blade member 16c, and the blade members 16a and 16b which open the least amount.

This variable opening of the blade members 16 also permits the medical practitioner to obtain clear access to the cervix of the patient. In this regard, the dilator 12 is opened, as hereinbefore described, and the curved surface 28 of the blade member 16c is used to push upwardly a forward portion of the uterus wall to provide a clearer view of the cervix. The movable collar 70 can then be rotated further in the direction of the arrow B causing only the lower blade member 16d to continue to open. This allows the medical practitioner a clear view of the cervix of the patient without obstruction thereof by the wall of the uterus of the patient. Since the blade members 16 open outwardly in all directions the patient's vagina is dilated uniformly in all directions. The blade members 16 thus provide a rigid liner to retain the patient's vagina in a dilated condition. This provides a tunnel for the medical practitioner for clear viewing and instrument insertion. This enables the medical practitioner to insert any required instruments into the patient's vagina through the opening 39a, passage 39 and the tunnel created by the blade members 16.

The opening 39a of the speculum 10 at the second (rear) end 38 of the support member 34 is relatively large and is of sufficient size for examination and instrument insertion by the medical practitioner. Its size does not depend on or vary with the extent of opening of the dilator 12. When transparent, the speculum 10 enables the medical practitioner to see the patient's vaginal wall which may assist in the examination.

When the dilator 12 is to be removed from the patient's vagina, the medical practitioner depresses the handle 54 (with his/her thumb) of his/her left hand which disengages the pawl 58 from the ratchet arrangement 94. The movable collar 70 moves back to the position shown in FIG. 1 under the collapsing influence of the vaginal wall of the patient on the blade members 16. The arcuate portions 78 thus cease to bear against the blade members 16. The blade members 16 return to their positions shown in FIG. 1, i.e. the closed position of the dilator 12. The dilator 12 may then be removed from the patient's vagina.

The gaps 32 between the blade members 16 prevent the flesh of the vaginal wall being pinched between the edges of adjacent blade members 16 when the dilator 12 is in its closed position.

Once removed, the speculum 10 may be discarded. Thus, the speculum 10 of the present invention may be a single use speculum.

The speculum 10 has been described as being used with the left hand of the medical practitioner.

However, the speculum in accordance with the present invention may also be made for use with the right hand.

Thus, a speculum for use with the right hand of a user has the directions of the curvatures of the arcuate portions 78 and the directions of taper of the substantially wedge shaped portions 62 (of the speculum 10) reversed. Thus, the movable collar would then be moved (using the right hand) in the opposite direction to arrow B to open the dilator 12. The ratchet arrangement 94 would be slightly repositioned and the pawl would be angled in reverse to the pawl 58 of the speculum 10.

In summary, the above parts would appear as mirror images in a speculum for right hand use.

The above description in relation to right handed use applies in a corresponding manner to the speculums of the second, third and fourth embodiments.

The speculum of the second embodiment (FIGS. 9 and 10) is used in a similar manner as hereinbefore described with reference to the speculum 10 of the first embodiment. However, the shape of the blade members 16' of the speculum of the second embodiment may be more suitable for some procedures involving examination of the uterus of a patient.

The speculum of the third embodiment (FIGS. 11 and 12) is used in a similar manner as hereinbefore described with reference to the speculum 10 of the first embodiment. The arcuate portion 78b", in combination with the arcuate portion 78a", enables variable opening of the blade members 16" of the dilator 12". However, as an alternative to the arcuate portion 78b" an arcuate portion 78b"a may be provided. The arcuate portion 78b"a has the same curvature as the arcuate portion 78a". Thus, the arcuate portions 78a" and 78b" a provide the same amount of opening of the blades 16" of the dilator 12". (In this regard, it is also possible to change the curvatures of the arcuate portions 78 of the speculum 10 such that they all have the same curvature. This provides the same amount of opening of the blades 16 of the dilator 12 of the speculum 10.)

The speculum of the second embodiment may be used as a vaginal speculum.

The speculum of the fourth embodiment (FIGS. 13 and 14) is used in a similar manner as hereinbefore described with reference to the speculum 10 of the first embodiment.

However, the provision of three blade members 16! makes it more suitable for use as a rectal (or anal) speculum. Further, a rectal speculum may also be provided by replacing the three blade members 16! with three blade members similar to the blade members 16' of the speculum of the second embodiment, but slightly larger in the transverse direction T!.

Preferably, a rectal speculum has three blade members which open the same amount.

Preferably, a vaginal speculum has four blade members which have variable opening.

However, a speculum in accordance with the present invention may be provided with any suitable number of blade members and with the same or variable opening depending upon its application, e.g. depending upon which body cavity it is intended to be used for.

The present invention provides a speculum that can be operated using one hand - insertion, dilation, locking, unlocking and removal can all be effected with one hand. Thus, the medical practitioner always has at least one hand free.

The speculum may be made for left or right handed use. The speculum of the present invention is compact. The speculum of the present invention may be made from a light-weight material and which does not cause discomfort to the patient, e.g. plastics. However, other materials are also suitable e.g. metal.

Preferably, the speculum is made of plastics which allows it to be readily made as a "single use" instrument and then discarded. This is important because the transfer of many diseases may not be preventable by mere sterilization of the instruments used.

Modifications and variations such as would be apparent to a skilled addressee are deemed within the scope of the present invention.

I claim:

1. A speculum comprising:

dilator means for insertion into a body cavity of a patient, said dilator means comprising at least two pivotal two blade members, each blade member being curved in a direction transverse to its length and having a rear terminating end which is provided with a substantially wedge shaped portion; and opening means being movable for opening said dilator means to dilate said body cavity, wherein said opening means is provided with arcuate portions which contact and bear against the substantially wedge shaped portions of said blade members when said opening means is moved in a first direction to cause said blade members to pivot such that said dilator means opens to dilate said body cavity.

2. A speculum according to claim 1, wherein said blade members are pivotally supported on support means and retained in place by a surrounding collar, said support means defining an opening at the rear of said speculum.

3. A speculum according to claim 1, wherein each said blade member is provided with a rear proximal part which includes said rear terminating end and a distal part with a shank-like portion therebetween, said distal part and said shank-like portion being narrower than said rear proximal part.

4. A speculum according to claim 2, wherein locking means is provided to retain said opening means in a selected position such that said dilator means is retainable at a selected amount of opening.

5. A speculum according to claim 1, wherein said opening means is provided with a handle to enable a user to move said opening means.

6. A speculum according to claim 1, wherein stop means is provided to limit the travel of said opening means when moved to open said dilator means.

7. A speculum according to claim 1, wherein said opening means comprises a collar.

8. A speculum according to claim 1, wherein said arcuate portions curve inwardly from the direction of an outer side of said opening means toward an inner side of said opening means.

9. A speculum according to claim 1, wherein said arcuate portions are of substantially the same curvature such that said blade members are able to pivot the same amount.

10. A speculum according to claim 1, wherein at least one of said arcuate portions has a curvature different from the curvature(s) of the other said arcuate portions such that said blade member which is contacted by said at least one arcuate portion is able to pivot a different amount.

11. A speculum according to claim 2, wherein said surrounding collar is provided with a handle for a user to hold said speculum.

12. A speculum according to claim 2, wherein said support means and said surrounding collar are connected by connection means extending therebetween.

13. A speculum according to claim 2, wherein said support means is provided with fulcrum means comprising curves surfaces and said blade members are provided with recesses which are contoured to, and mate with, said curved surfaces of said fulcrum means such that said blade members are pivotal.

14. A speculum according to claim 2, wherein said opening means is provided on said support means.

15. A speculum according to claim 2, wherein said blade members are pivotally supported around the periphery of said support means and extend outwardly therefrom in adjacent manner when said dilator means is closed.

16. A speculum according to claim 2, wherein said support means comprises a short tubular member.

17. A speculum according to claim 3, wherein at least two of said blade members are provided with curved surface portions at their respective distal parts and at least one of said two blade members has a notch in the edge of said curved surface portion.

18. A speculum according to claim 3, wherein said blade members are substantially triangular and taper to respective narrow inwardly curved tips at their distal parts.

19. A specular according to claim 3, wherein three said blade members are provided.

20. A speculum according to claim 4, wherein said locking means comprises a pawl means and ratchet means, said pawl means provided on a lug extending from said support means and said ratchet means is provided on said opening means such that said opening means is readily movable to open said dilator means but said lug means must be depressed to disengage said pawl means from said ratchet means to enable said dilator means to close.

21. A speculum according to claim 1, wherein said substantially wedge shaped portions are provided with angled base portions which are received in angled recess base portions of respective said arcuate portions to prevent said blade members from pivoting to open said dilator means.

22. A speculum according to claim 10, wherein four said blade members are provided comprising an upper blade member, a lower blade member and two side blade members and the said arcuate portions which contact said side blade members have a first curvature, the said arcuate portion which contacts said upper blade member has a second curvature and the said arcuate portion which contacts said lower blade member has a third curvature, said third curvature being greater than said second curvature and said second curvature being greater than said first curvature such that said lower blade member is able to pivot the greatest amount, followed by said upper blade member and said side blade members are able to pivot the least amount.

23. A speculum according to claim 10, wherein two said blade members are provided comprising an upper blade member and a lower blade member, and the said arcuate portion which contacts said upper blade member has a first curvature and the said arcuate portion which contacts said lower blade member has a second curvature and said second curvature is greater than said first curvature such that said lower blade member is able to pivot the greater amount.

24. A speculum according to claim 12, wherein said blade members are provided with tapered edges at the rear portions thereof and spaces are formed between respective said tapered edges of adjacent said blade members, and said connection means are provided in said spaces.

25. A speculum according to claim 14, wherein said support means is provided at one end with flange means and opening means is retained between said surrounding collar and said flange means.

26. A speculum according to claim 18, wherein one of said at least two blade members is longer than the other.

27. A speculum according to claim 17, wherein two further said blade members are provided with rounded edges at their respective distal parts and are shorter than said at least two blade members.

28. A speculum comprising:

dilator means for insertion into a body cavity of a patient, said dilator means comprising at least two blade members;

support means about which said blade members are disposed and on which said blade members are pivotally supported;

a collar surrounding at least a portion of each blade member, so that the blade members are pivotally retained between said support means and said collar, with a rear terminating end of each blade member extending beyond said collar and being provided with a substantially wedge shaped portion; and opening means rotatably provided on said collar and including arcuate portions which contact and bear against the rear terminating end of respective blade members at said substantially wedge shaped portions when said opening means is rotated in a first direction to cause said blade members to pivot on said support means such that said dilator means opens and dilates said body cavity.

29. A speculum according to claim 28 wherein at least one of said arcuate portions has a curvature different from the curvature(s) of the other of said arcuate portions such that said blade member which is contacted by said at least one arcuate portion is able to pivot a different amount.

30. A speculum according to claim 28 further comprising locking means to retain said opening means in a selected position such that said dilator means is retainable at a selected amount of opening.

31. A speculum according to claim 30 wherein said locking means comprises a pawl means and ratchet means, said pawl means provided on a lug extending from said support means and said ratchet means is provided on said opening means such that said opening means is readily rotatable to open said dilator means but said lug means must be depressed to disengage said pawl means from said ratchet means to enable said dilator to close.

32. A speculum according to claim 28 wherein said substantially wedge shaped portions are provided with angled base portions which are received in angled recess base portions of respective arcuate portions to prevent said blade members from pivoting to open said dilator means.

33. A speculum according to claim 28 wherein said support means is provided with fulcrum means comprising curved surfaces and said blade members are provided with recesses which are contoured to, and mate with, said curved surfaces of said fulcrum means such that said blade members are pivotal.

34. A speculum according to claim 28, wherein four said blade members are provided comprising an upper blade member, a lower blade member and two side blade members and the said arcuate portions which contact said side blade members have a first curvature, the said arcuate portion which contacts said upper blade member has a second curvature and the said arcuate portion which contacts said lower blade member has a third curvature, said third curvature being greater than said second curvature and said second curvature being greater than said first curvature such that said lower blade member is able to pivot the greatest amount, followed by said upper blade member and said side blade members are able to pivot the least amount.

* * * * *